(12) United States Patent
Zhang

(10) Patent No.: US 8,015,872 B2
(45) Date of Patent: Sep. 13, 2011

(54) SURFACE ACOUSTIC WAVE BASED HUMIDITY SENSOR APPARATUS WITH INTEGRATED SIGNAL CONDITIONING

(75) Inventor: Wenwei Zhang, Bellshill (GB)

(73) Assignee: Honeywell International Inc., Morristown, NJ (US)

( * ) Notice: Subject to any disclaimer, the term of this patent is extended or adjusted under 35 U.S.C. 154(b) by 336 days.

(21) Appl. No.: 12/207,017

(22) Filed: Sep. 9, 2008

(65) Prior Publication Data

US 2010/0058857 A1  Mar. 11, 2010

(51) Int. Cl.
*G01N 27/12* (2006.01)
(52) U.S. Cl. .................................... 73/335.02
(58) Field of Classification Search ............... 73/335.02; 338/35
See application file for complete search history.

(56) References Cited

U.S. PATENT DOCUMENTS

| | | | | |
|---|---|---|---|---|
| 4,221,129 | A | 9/1980 | Sidebottom et al. | 73/336.5 |
| 4,895,017 | A * | 1/1990 | Pyke et al. | 73/24.06 |
| 5,189,902 | A | 3/1993 | Groeninger | 73/24.06 |
| 5,369,995 | A | 12/1994 | Scheinbeim et al. | 73/335.02 |
| 6,724,612 | B2 | 4/2004 | Davis et al. | 361/328 |
| 6,867,602 | B2 | 3/2005 | Davis et al. | 324/664 |
| 7,373,819 | B2 | 5/2008 | Engler et al. | 73/335.03 |
| 2002/0047495 | A1 * | 4/2002 | Nakano et al. | 310/313 R |
| 2005/0247106 | A1 | 11/2005 | Speldrich et al. | 73/29.01 |
| 2005/0247107 | A1 | 11/2005 | Speldrich et al. | 73/29.01 |
| 2006/0201247 | A1 | 9/2006 | Speldrich et al. | 73/335.06 |
| 2006/0225488 | A1 | 10/2006 | Speldrich | 73/29.01 |
| 2006/0237551 | A1 | 10/2006 | Engler et al. | 236/44 C |
| 2008/0061802 | A1 | 3/2008 | Alimi et al. | 324/689 |
| 2008/0084135 | A1 * | 4/2008 | Ramsesh et al. | 310/313 R |
| 2009/0267761 | A1 * | 10/2009 | Georgescu et al. | 340/540 |

FOREIGN PATENT DOCUMENTS

JP       61128138 A  *  6/1986

* cited by examiner

*Primary Examiner* — Hezron Williams
*Assistant Examiner* — Tamiko D Bellamy
(74) *Attorney, Agent, or Firm* — Shumaker & Sieffert, P.A.

(57) ABSTRACT

A SAW-based humidity sensor apparatus with integrated signal conditioning on the same substrate. A micro-electronic circuit can be processed at a silicon substrate to obtain on-chip signal conditioning internally and the silicon substrate can be covered with a protective layer of, for example, silicon nitride. Surface acoustic wave media (e.g., a ZnO film) can be coated on top of the protective layer. A humidity sensitive film and two sets of interdigital transducers can then be deposited on the surface acoustic wave media. The humidity sensitive film absorbs moisture and changes the receiving frequency at the two sets of interdigital transducers. The output from the two sets of interdigital transducers can be processed by the micro-electronic circuit, which eliminates common mode noise and generates an output signal proportional to the humidity value tested.

20 Claims, 2 Drawing Sheets

SURFACE ACOUSTIC WAVE BASED HUMIDITY SENSOR APPARATUS WITH INTEGRATED SIGNAL CONDITIONING

TECHNICAL FIELD

Embodiments are generally related to sensing devices and applications. Embodiments are also related to humidity sensors and SAW (Surface Acoustic Wave) sensing devices. Embodiments are further related to SAW-based humidity sensor with integrated signal conditioning.

BACKGROUND OF THE INVENTION

Humidity sensors are widely utilized for humidity and air quality measurement in a variety of applications (e.g., automotive for comfort, safety and power train, home appliances for moisture and temperature control, energy efficiency, humidity switches, HVAC, etc.). Humidity can be measured utilizing a number of techniques such as, for example, wet bulb psychrometer, chilled mirror dew point, saturated salt solutions, resistive RH sensors, capacitive RH sensors, and SAW-based humidity.

The majority of prior art capacitive humidity sensors with on-chip signal conditioning internally connected with a humidity capacitive element possess advantages such as a high signal-to-noise rate, low cost, and small size due to the elimination of wire connections between the capacitive element and separate supporting circuitry. Such capacitive humidity sensors, however, possess a number of disadvantages such as a slow response time, inherent accuracy issues (e.g., 2% or less), device degradation over a long period (e.g., over a 5 year period) and a relatively high hysteresis. These disadvantages can constrain the application of the capacitive humidity sensor in high-end applications such as, for example, weather stations, instrumentation and industrial control in semiconductor foundries.

One solution to this problem involves utilizing a SAW-based humidity sensor with approximately a 1 second response time and 1% accuracy for high-end applications. A SAW sensor, however, utilizes a bulk piezoelectric material (e.g., LiNbO3, LiTaO3, quartz etc.) as a substrate to transform the surface acoustic wave. The piezoelectric materials are not semiconductor circuitry compatible materials, although they are good acoustic transmission materials.

Hence, it is not possible to integrate the signal conditioning circuitry on the same chip, as SAW sensing devices rely on piezoelectric materials to transform the electrical energy to surface acoustic waves and to interrogate with the humidity sensitive film and also sense the humidity value tested. Therefore, separate signal conditioning circuitry must be developed. Additionally, the SAW sensing element and signal conditioning circuitry must be packaged and bonded together to generate a meaningful output, which is proportional to the humidity value tested. Such a solution possesses inherent disadvantages such as, for example, a low signal-to-noise and is relatively complex and expensive to package.

SAW-based sensors to date also include one set of interdigital (IDT) transducers and a humidity sensitive film deposited on the top of a surface acoustic wave media. When the humidity sensitive film absorbs the moisture, the mass will change, thereby altering the frequency at the receiving IDT. However, because the output frequency of the IDT is also sensitive to temperature and pressure, a single IDT set cannot distinguish between differences in pressure, temperature and humidity values.

Based on the foregoing, it is believed that a need exists for an improved SAW-based humidity sensor with integrated signal conditioning that is capable of being configured and/or located on the same substrate. A need also exits for designing a common mode delay line in order to eliminate common mode noise, as described in greater detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensing device and applications thereof.

It is another aspect of the present invention to provide for an improved SAW-based humidity sensor capable of integrated signal conditioning.

It is a further aspect of the present invention to provide for a SAW-based humidity sensor having common mode delay lines with two sets of IDTs in order to eliminate common mode noise.

It is yet another aspect of the present invention to provide for a method of forming a SAW-based humidity sensor.

The aforementioned aspects and other objectives and advantages can now be achieved as described herein. A SAW-based humidity sensor apparatus with integrated signal conditioning on the same substrate and method forming such an apparatus is disclosed. Micro-electronic circuitry can be processed on a substrate (e.g., silicon) to obtain on-chip signal conditioning internally. The substrate can be covered with a protective layer (e.g., silicon nitride layer) to protect the micro-electronic circuitry from damage. Surface acoustic wave media (e.g., ZnO film) can be then coated on top of the protective layer. A humidity sensitive film and two sets of IDTs can then be deposited on the surface acoustic wave media. The humidity sensitive film absorbs moisture and alters the receiving frequency at the two sets of IDTs. The output from the two sets of IDTs can be processed by the micro-electronic circuitry, which eliminates common mode noise and generates an output signal proportional to the humidity value tested.

The thickness of the ZnO film, for example, can be optimized to raise the coupling rate of the surface acoustic wave (s) and to improve the resolution and sensitivity of the sensor. The two sets of IDTs can include a reference IDT set and a sensing IDT set. The micro-electronic circuitry can be further configured to include a mixer, an intermediate filter and a phase lock loop component. The output of the sensing IDT set and the reference IDT set can be fed into the mixer. The receiving frequency at the sensing IDT set and the reference IDT set changes when the pressure and temperature change.

The common mode noise can be eliminated by the mixer and hence, the output frequency is only proportional to the humidity value tested. Then, the frequency signal can be fed into the intermediate filter and phase lock loop component. The frequency signal can be converted into an amplitude signal for final application. The disclosed single chip solution with SAW-based humidity sensor integrated with micro-electronic circuitry therefore provides a quick response time (e.g., <1 S) and better accuracy (e.g., 1%), which is suitable for instrumentation in high-end applications.

BRIEF DESCRIPTION OF THE DRAWINGS

The accompanying figures, in which like reference numerals refer to identical or functionally similar elements through- FIG. 1 illustrates a cross sectional view of a SAW-based humidity sensor apparatus, which can be implemented in accordance with a preferred embodiment.

DETAILED DESCRIPTION

The particular values and configurations discussed in these non-limiting examples can be varied and are cited merely to illustrate at least one embodiment and are not intended to limit the scope thereof.

Figure 1:
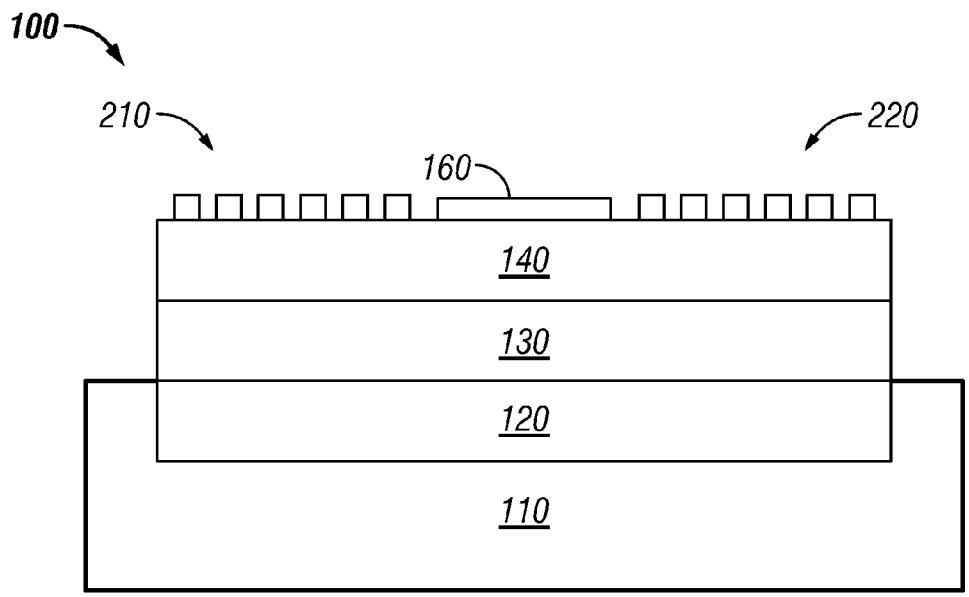

FIG. 1 illustrates a cross sectional view of a SAW-based humidity sensor apparatus 100, which can be implemented in accordance with a preferred embodiment. The SAW-based humidity sensor apparatus 100 generally includes a microelectronic circuit 120 that can be processed at a silicon substrate 110. A protective layer 130 of, for example, silicon nitride, can be deposited on top of the micro-electronic circuit 120 to protect the micro-electronic circuit 120 from damage. The micro-electronic circuit 120 can be processed at the silicon substrate 110, which is compatible with normal electronic processes.

Surface acoustic wave media 140 (e.g., a ZnO film) can then be deposited on top of the protective layer 130. The ZnO film thus acts as surface acoustic wave media. Acoustic waves are generally distinguished from their velocities and displacement directions; many combinations are possible, depending on the material and boundary conditions. The thickness of the surface acoustic wave media 140 can be optimized to optimize the coupling efficiency between electrical energy converted to mechanical energy.

In general, the surface acoustic wave media 140 can be utilized as surface acoustic wave media due to its piezoelectric nature. ZnO has a porous surface and is a piezoelectric material with a low phase velocity. This implies that ZnO can increase the electromechanical coupling coefficient more than other deposited materials. The sensor apparatus 100 further includes two sets of IDTs 210 and 220 that can be placed on the surface acoustic wave media 140 which can be utilized to sense the humidity in the medium. A humidity sensitive film 160 can be deposited on the top of the surface acoustic wave media 140, which can absorb the moisture and change its mass. When the humidity sensitive film 160 absorbs the moisture, the mass of the humidity sensitive film 160 will change, changing the receiving frequency at the IDTs 210 and 220. The IDT sets 210 and 220 can distinguish the differences of pressure, temperature and humidity value. As the acoustic wave propagates through or on the surface of the humidity sensitive film 160, any changes to the characteristics of the propagation path affect the velocity and/or amplitude of the wave. The changes in velocity can be monitored by measuring the frequency or phase characteristics of the sensor apparatus 100 and can then be correlated to the humidity being measured.

Figure 2:
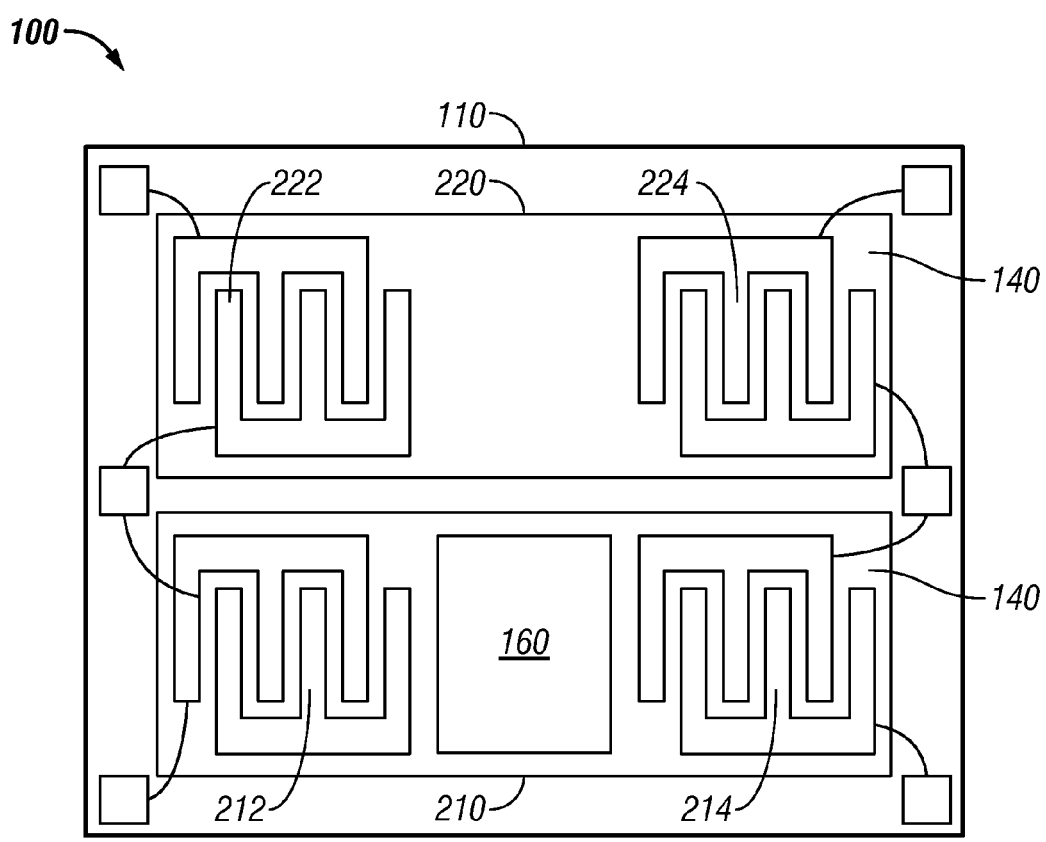
FIG. 2 illustrates a top view of a SAW-based humidity sensor apparatus, which can be implemented in accordance with a preferred embodiment.

FIG. 2 illustrates a top view of the SAW-based humidity sensor apparatus 100, which can be implemented in accordance with a preferred embodiment. Note that in FIGS. 1-4, identical or similar parts are generally indicated by identical reference numerals. The SAW-based humidity sensor apparatus 100 includes two sets of IDTs such as a sensing IDT set 210 and a reference IDT set 220, which can be deposited on top of the surface acoustic wave media 140 in order to form a common mode design. The sensing IDT set 210 includes an input IDT 212 and an output IDT 214 generally placed on the surface acoustic wave media 140, which can be utilized for acoustic wave propagation. The reference IDT set 220 includes an input IDT 222 and an output IDT 224 generally placed on the surface acoustic wave media 140, which can be utilized for acoustic wave propagation.

The reference IDT set 220 possess similar visco-elastic properties as sensing IDT set 210, but not sensitive to the humid medium. The reference (non-sensing) IDT set 220 can have the same temperature and pressure behavior as the sensing IDT set 210. The reference IDT set 220 can be utilized to obtain symmetry between the sensing IDT set 210 and the reference IDT set 220 of the SAW-based humidity sensor apparatus 100. The output frequency of the IDT sets 210 and 220 can be sensitive to external factors such as temperature and pressure. Thus, a common system can be designed as depicted in FIG. 2 with the sensing IDT set 210 and the reference IDT set 220. When the pressure and temperature change, the receiving frequency at both sensing and reference IDT sets 210 and 220 also changes. The output signals from the IDT sets 210 and 220 can be processed appropriately by the micro-electronic circuit 120 in order to eliminate common mode noise and generate an output signal proportional to the humidity value tested.

Figure 3:
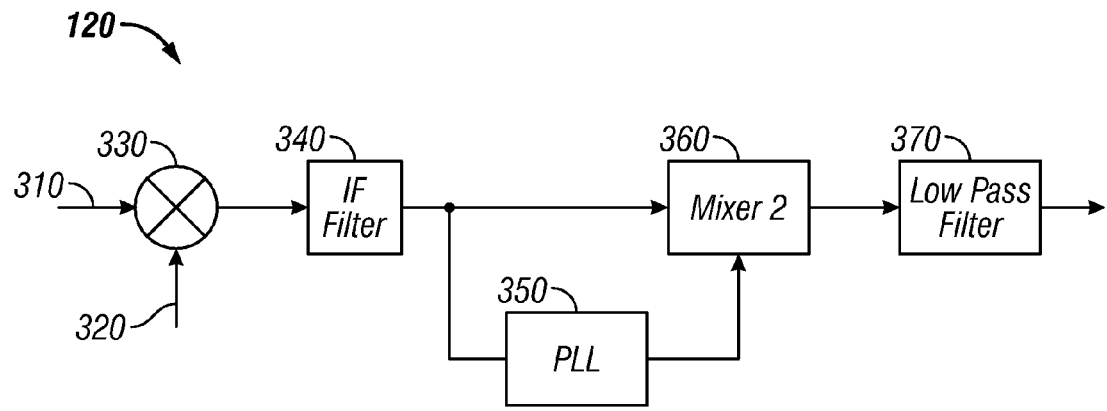
FIG. 3 illustrates a schematic block diagram of a microelectronic circuitry integrated with the SAW-based humidity sensor apparatus, which can be implemented in accordance with a preferred embodiment.

FIG. 3 illustrates a schematic block diagram of the microelectronic circuit 120 associated with the SAW sensor apparatus 100, which can be implemented in accordance with the preferred embodiment. The micro-electronic circuit 120 includes a mixer 330, an IF (intermediate filter) filter 340, a PLL (phase-locked loop) 350 and a low pass filter 370. The micro-electronic circuit 120 can be utilized to process the output of the IDTs 210 and 220 of the SAW-based humidity sensor apparatus 100. A sensing output 310 of the sensing IDT set 210 and a reference output 320 of the reference IDT set 220 can be fed into the mixture 330. The mixture 330 can be utilized to perform a frequency subtraction between the sensing output 310 and the reference output 320. Thus, when the SAW sensor apparatus 100 is subject to pressure and temperature causing change of output frequency of IDT 210 and 220, both IDT are proportional with each other.

The mixture 330 can be utilized to eliminate common mode noise such as temperature and pressure noise in the frequencies and generate an output, which is proportional to the humidity value tested. Thereafter, the output of the mixture 330 can be fed into an intermediate filter 340 and a phase lock loop component 350 and converted into an amplitude signal for final application. A phase-locked loop or phase lock loop component 350 can be a control system which generates a signal that possesses a fixed relation to the phase of a reference signal. A phase-locked loop component 350 responds to both the frequency and the phase of the input signals, automatically raising or lowering the frequency of a controlled oscillator until it is matched to the reference in both frequency and phase. The amplitude signal from the phase lock loop component 350 and intermediate filter 340 can be fed to a second mixer 360 for frequency subtraction functions. Later, the amplitude signal can be fed to a low pass filter 370. The low-pass filter 370 can be configured as a filter that passes low-frequency signals, but attenuates (i.e., reduces the amplitude of) signals with frequencies higher than the cutoff frequency. The micro-electronic circuit 120 integrated with the silicon substrate 110 can transform the output signal which is only proportional to the humidity value tested.

Figure 4:
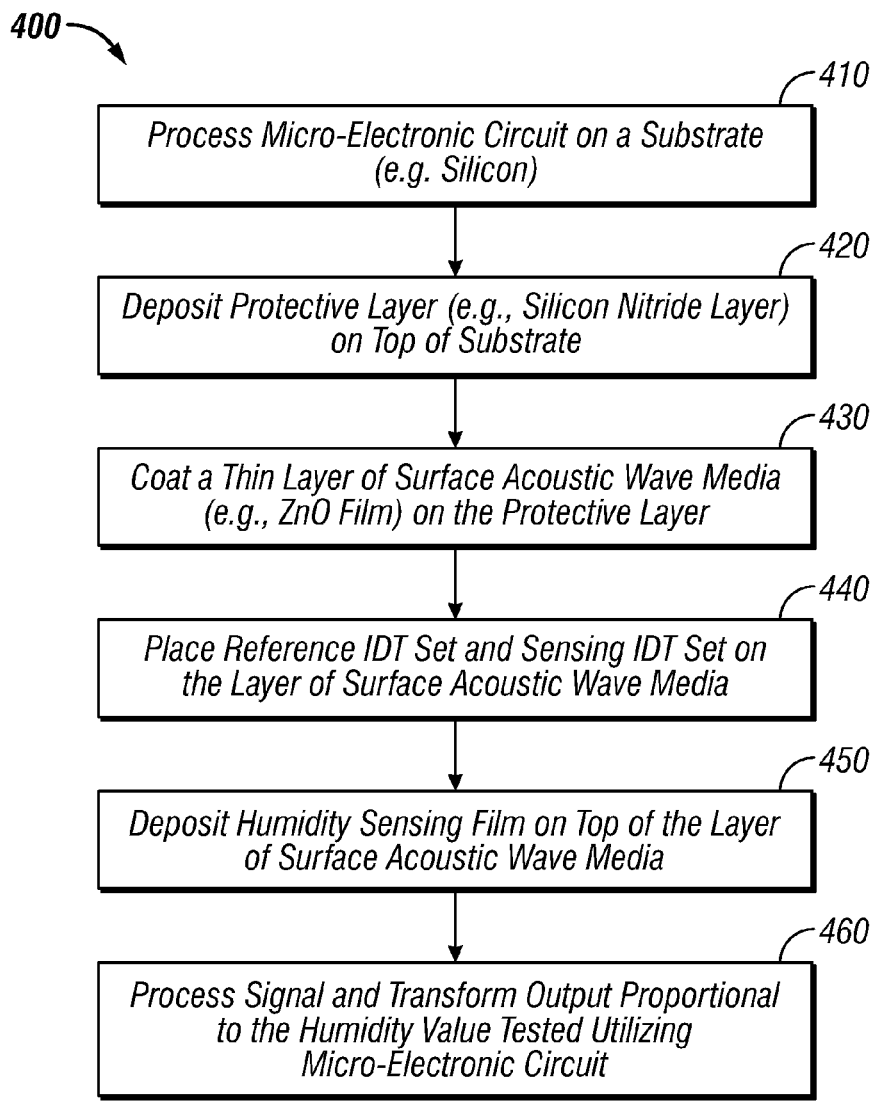
FIG. 4 illustrates a high-level flow chart illustrating logical operational steps of a method for processing a SAW-based humidity sensor apparatus with integrated signal conditioning on the same substrate, which can be implemented in accordance with an alternative embodiment.

FIG. 4 illustrates a detailed flow chart of operation illustrating processing steps of a method 400 for processing a SAW-based humidity sensor apparatus 100 with integrated signal conditioning circuit 120 on the same substrate 110, which can be implemented in accordance with a preferred embodiment. The micro-electronic circuit 120 can be processed on the silicon substrate 110, as illustrated at block 410. The protective layer 130 can be deposited on top of the silicon substrate 110 to protect the electronic circuit 120 from damage, as depicted at block 420. Thereafter, as illustrated at block 430, a thin layer of ZnO (zinc oxide) film 140 can be deposited on the protective layer 130. The reference layer IDT set 220 and the sensing layer IDT set 210 can be placed on the surface acoustic wave media 140, as indicated at block 440.

The humidity sensitive film 160 can then be deposited on the top of surface acoustic wave media 140, as depicted at block 450. The humidity sensitive film 160 absorbs the moisture and changes the receiving frequency of the IDT sets 210 and 220 when the pressure and temperature changes. The micro-electronic circuit 120 can be utilized to process the signal from the IDT sets 210 and 220 and transform the output proportional to the tested humidity value, as illustrated at block 460. The mixture 330 associated with the micro-electronic circuit 120 can be utilized to eliminate common mode noise and the intermediate filter 340 and the phase lock loop component 350 converts the frequency signal into an amplitude signal for final application.

The SAW-based humidity sensor apparatus 100 integrated with the micro-electronic circuit 120, therefore, provides a quick response time (e.g., <1 S) and better accuracy (e.g., 1%), which is suitable for instrumentation applications in high-end environments. Further, the single chip solution provides higher signal-to-noise, low cost packaging and a small size. The common mode design with two sets of IDTs 210 and 220 eliminates common mode noise, such as temperature and pressure noise with respect to the humidity value tested. The thickness of the surface acoustic wave media 140 can be optimized to raise coupling rate of surface acoustic wave.

Based on the foregoing, it can be appreciated that the humidity sensor apparatus 100 as disclosed generally includes integrated signal conditioning capabilities. Such an apparatus includes the use of the micro-electronic circuit 120 processed on a substrate to provide on-chip signal conditioning internally, such that the substrate is covered with a protective layer to protect the micro-electronic circuit 120. The disclosed humidity sensor apparatus 100 also includes a film of surface acoustic wave media coated on top of the protective layer to couple with a surface acoustic wave, such that the thickness of the film is optimized to raise a coupling rate of the surface acoustic wave and to improve the resolution and sensitivity thereof. The humidity sensor apparatus 100 can also include two or more sets of interdigital transducers and a humidity-sensitive film deposited on top of the film and associated with the micro-electronic circuit 120. In this manner, the micro-electronic circuit 120 can process the frequency signal output from the two sets of interdigital transducers to thereby eliminate common mode noise from, for example, temperature, pressure, vibration, electronic-magnetic fields and other external interferences, and generate an output signal only proportional to the humidity value tested, thereby providing a single-chip solution with respect to the humidity sensor apparatus 100 that includes a high signal-to-noise, a quick response time, and enhanced sensing accuracy.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A humidity sensor apparatus with integrated signal conditioning, said apparatus comprising:
   a micro-electronic circuit processed on a substrate to provide on-chip signal conditioning internally, wherein said substrate is covered with a protective layer to protect said micro-electronic circuit;
   a film of surface acoustic wave media coated on top of said protective layer to couple with a surface acoustic wave, wherein a thickness of said film of surface acoustic wave media is configured to raise a coupling rate of said surface acoustic wave and to improve a resolution and a sensitivity thereof; and
   at least two sets of interdigital transducers and a humidity-sensitive film deposited on top of said film of surface acoustic wave media and associated with said micro-electronic circuit, wherein said micro-electronic circuit processes a frequency signal output from said at least two sets of interdigital transducers to thereby eliminate common mode noise from external interference and generate an output signal proportional only to a humidity value tested, thereby providing a single-chip solution with respect to said humidity sensor apparatus that includes a high signal-to-noise, a quick response time, and an enhanced sensing accuracy.

2. The apparatus of claim 1 wherein said substrate comprises silicon.

3. The apparatus of claim 1 wherein said protective layer comprises a silicon nitride layer.

4. The apparatus of claim 1 wherein said film of surface acoustic wave media comprises ZnO.

5. The apparatus of claim 1 wherein said at least two sets of interdigital transducers comprises a sensing interdigital transducer set and a reference interdigital transducer set.

6. The apparatus of claim 1 wherein said micro-electronic circuit further comprises:
   a mixer for eliminating said common mode noise from said frequency signal of said at least two sets of interdigital transducers; and
   an intermediate filter and a phase lock loop component electronically in communication with said mixer, wherein said intermediate filter and said phase lock loop component convert said output signal into an amplitude signal for a final sensing application thereof.

7. The apparatus of claim 1 wherein said micro-electronic circuit further comprises a low pass filter.

8. The apparatus of claim 1 wherein said humidity sensitive film absorbs moisture and changes a frequency associated with said at least two sets of interdigital transducers.

9. A humidity sensor apparatus with integrated signal conditioning, said apparatus comprising:
   a micro-electronic circuit processed on a substrate to provide on-chip signal conditioning internally, wherein said substrate is covered with a protective layer to protect said micro-electronic circuit;

a film of surface acoustic wave media coated on top of said protective layer to couple with a surface acoustic wave, wherein a thickness of said film of surface acoustic wave media is configured to raise a coupling rate of said surface acoustic wave and to improve a resolution and a sensitivity thereof; and at least two sets of interdigital transducers and a humidity-sensitive film deposited on top of said film of surface acoustic wave media and associated with said micro-electronic circuit, wherein said at least two sets of interdigital transducers comprises a sensing interdigital transducer set and a reference interdigital transducer set and wherein said micro-electronic circuit processes a frequency signal output from said at least two sets of interdigital transducers to thereby eliminate common mode noise from external interference and generate an output signal proportional only to a humidity value tested, thereby providing a single-chip solution with respect to said humidity sensor apparatus that includes a high signal-to-noise, a quick response time, and an enhanced sensing accuracy.

10. The apparatus of claim 9 wherein:
said substrate comprises silicon;
said protective layer comprises a silicon nitride layer; and
said film of surface acoustic wave media comprises ZnO.

11. The apparatus of claim 9 wherein:
said micro-electronic circuit further comprises:
 a mixer for eliminating said common mode noise from said frequency signal of said at least two sets of interdigital transducers;
 an intermediate filter and a phase lock loop component electronically in communication with said mixer, wherein said intermediate filter and said phase lock loop component convert said output signal into an amplitude signal for a final sensing application thereof; and
said micro-electronic circuit further comprises a low pass filter.

12. The apparatus of claim 10 wherein said humidity sensitive film absorbs moisture and changes a frequency associated with said at least two sets of interdigital transducers.

13. A method of forming a humidity sensor apparatus with integrated signal conditioning, said method comprising:
providing a substrate;
configuring a micro-electronic circuit on said substrate to provide on-chip signal conditioning internally;
covering said substrate with a protective layer to protect said micro-electronic circuit;
coating a film of surface acoustic wave media on top of said protective layer to couple with a surface acoustic wave, wherein a thickness of said film of surface acoustic wave media is configured to raise a coupling rate of said surface acoustic wave and to improve a resolution and a sensitivity thereof; and
depositing at least two sets of interdigital transducers and a humidity-sensitive film on top of said film of surface acoustic wave media and associating said at least two sets of interdigital transducers and said humidity-sensitive film with said micro-electronic circuit, wherein said micro-electronic circuit processes a frequency signal output from said at least two sets of interdigital transducers to thereby eliminate common mode noise from external interference and generate an output signal proportional only to a humidity value tested, thereby providing a single-chip solution with respect to said humidity sensor apparatus that includes a high signal-to-noise, a quick response time, and an enhanced sensing accuracy.

14. The method of claim 13 further comprising configuring said substrate from silicon.

15. The method of claim 13 further comprising configuring said protective layer to comprise a silicon nitride layer.

16. The method of claim 13 further comprising configuring said film of surface acoustic wave media from ZnO.

17. The method of claim 13 further comprising configuring said at least two sets of interdigital transducers to include a sensing interdigital transducer set and a reference interdigital transducer set.

18. The method of claim 13 configuring said micro-electronic circuit to further comprise:
a mixer for eliminating said common mode noise from said frequency signal of said at least two sets of interdigital transducers; and
an intermediate filter and a phase lock loop component electronically in communication with said mixer, wherein said intermediate filter and said phase lock loop component convert said output signal into an amplitude signal for a final sensing application thereof.

19. The method of claim 13 configuring said micro-electronic circuit to include a low pass filter.

20. The method of claim 13 further comprising configuring said humidity-sensitive film to absorb moisture and change a frequency associated with said at least two sets of interdigital transducers.

* * * * *